United States Patent [19]

Hirai

[11] 4,433,154

[45] Feb. 21, 1984

[54] BIS(CARBOXAMIDE) DERIVATIVES

[75] Inventor: Kentaro Hirai, Kyoto, Japan

[73] Assignee: Shionogi & Company, Limited, Osaka, Japan

[21] Appl. No.: 328,444

[22] Filed: Dec. 7, 1981

[51] Int. Cl.³ .................. C07D 277/38; C07D 417/12; C07D 403/12; C07D 405/12

[52] U.S. Cl. ...................................... 548/195; 542/416; 546/280; 546/281; 546/783; 546/284; 548/184; 548/187; 548/198; 548/517; 548/523; 548/527; 548/571; 549/60; 549/62; 549/63; 549/65; 549/68; 549/473; 549/494; 549/501; 564/154; 564/155; 564/156; 564/157; 424/210; 424/275; 424/276; 424/271; 424/285; 424/320; 424/324

[58] Field of Search ................ 542/416; 548/198, 184, 548/336, 187, 523, 517, 571, 527; 546/280, 281, 283, 284; 549/68, 60, 473, 494, 62, 63, 65, 501; 564/154, 155, 156, 157; 424/320, 324, 270, 275, 276, 285, 274

[56] References Cited

U.S. PATENT DOCUMENTS 4,366,164  12/1982  Clitherow ........................ 424/267

FOREIGN PATENT DOCUMENTS 2626315  12/1976  Fed. Rep. of Germany .
51-114930  10/1976  Japan .

Primary Examiner—Robert Gerstl
Attorney, Agent, or Firm—Wenderoth, Lind & Ponack

[57]  ABSTRACT

Bis(carboxamide) derivatives being useful as histamine $H_2$ receptor antagonists or anti-peptic ulcer agents are provided from certain dicarboxylic acid derivatives.

17 Claims, No Drawings

BIS(CARBOXAMIDE) DERIVATIVES

BACKGROUND OF THE INVENTION (1) Field of the Invention

The present invention relates to histamine $H_2$ receptor antagonists, bis(carboxamide) derivatives.

(2) Description of the Prior Art

As the histamine $H_2$ blockers, thiaburimamide, metiamide, oxaburimamide, urea isostere, nitroguanidine isostere, cimetidene, the SK&F 92456, etc. have been known. The above compounds bind to histamine $H_2$ receptor competitively with histamine to suppress the histamine $H_2$ effect.

Although the compounds in the present invention have similar effect as mentioned above, their structures are quite different from those of the above prior art compounds.

REFERENCE (1) German Pat. Nos. 2,344,779.
(2) G. J. Durant, C. R. Ganellin, et al., J. Med. Chem., 20, 901 (1977).
(3) C. R. Ganellin, J. Med. Chem., 24, 913 (1981).
(4) R. W. Brimblecombe, G. J. Durant, et al., J. Int. Med. Res., 3, 86 (1975).

SUMMARY OF THE INVENTION

Compounds of the formula:

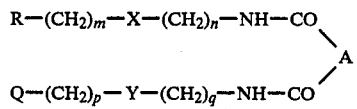

(wherein

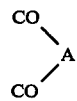

is dicarboxylic acid residue;
R and Q, being the same or different, each is aryl or 5- or 6-membered heterocycle respectively substituted by alkyl, guanidino, and/or

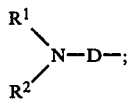

$R^1$ and $R^2$ each is alkyl or $R^1$ and $R^2$, taken together with the adjacent nitrogen, form 4- to 7-membered heterocycle;
D is alkylene;
X and Y each is oxa, thia, or methylene;
m and p each is 0 or 1; and
n and q each is an integer of 1 to 4)
or its pharmaceutically acceptable acid addition salts, which are useful in treatment of diseases caused by histamine at $H_2$ receptor, such as peptic ulcer.

DESCRIPTION OF THE PREFERRED EMBODIMENT

This invention relates to compounds of the formula:

(wherein

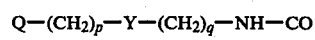

is dicarboxylic acid residue;
R and Q, being the same or different, each is $C_6$–$C_{10}$ aryl or 5- or 6-membered heterocycle respectively substituted by $C_1$–$C_3$ alkyl, guanidino, and/or

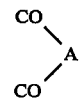

$R^1$ and $R^2$ each is $C_1$–$C_3$ alkyl or $R^1$ and $R^2$, taken together with the adjacent nitrogen, form 4- to 7-membered heterocycle;
D is $C_1$–$C_5$ alkylene;
X and Y each is oxa, thia, or methylene;
m and p each is 0 or 1; and
n and q each is an integer of 1 to 4)
or its pharmaceutically acceptable acid addition salts.

In the above dicarboxylic acid residue, A is a single bond or $C_1$–$C_5$ alkylene, $C_2$–$C_6$ alkenylene, $C_4$–$C_6$ cycloalkylene, $C_6$–$C_7$ cycloalkenylene, $C_8$–$C_{12}$ aralkylene, $C_6$–$C_{10}$ arylene, or a bivalent group derived from 5- or 6-membered heterocycle, in which the carbon chain may be separated by an oxygen or sulphur, and all the above groups may have substituents selected from $C_1$–$C_3$ alkyl, $C_1$–$C_3$ alkoxy, amino and oxo.

The terms used in the above definition are concretely illustrated as follows.

$C_1$–$C_3$ alkyl is methyl, ethyl, propyl, or isopropyl;
$C_6$–$C_{10}$ aryl is phenyl, tolyl, xylyl, naphthyl, etc.;
5- or 6-membered heterocycle is furyl, thienyl, imidazolyl, thiazolyl, isothiazolyl, oxazolyl, isoxazolyl, pyrrolyl, pyrazolinyl, thiadiazolyl, oxadiazolyl, triazolyl, triazinyl, pyridyl, pyrimidinyl, pyridazinyl, etc.;
4- to 7-membered heterocycle is azetidinyl, pyrrolidinyl, piperidinyl, morpholinyl, piperazinyl, 1H-hexahydroazepinyl, etc.;
$C_1$–$C_5$ alkylene is methylene, ethylidene, ethylene, propylidene, propylene, trimethylene, isopropylidene, butylidene, ethylethylene, 1-methyltrimethylene, tetramethylene, 1,2-dimethylethylene, 2-methyltrimethylene, etc.;
$C_2$–$C_6$ alkenylene is vinylene, propenylene, butenylene, pentenylene, butadienylene, pentadienylene, etc.;
$C_4$–$C_6$ cycloalkylene is a bivalent group derived from cycloalkanes such as cyclobutane, cyclopentane, and cyclohexane.
$C_6$–$C_7$ cycloalkenylene is a bivalent group derived from cyclohexene, cyclohexadiene, cyclopentene, cycloheptadiene, or cycloheptatriene.
$C_8$–$C_{12}$ aralkylene is

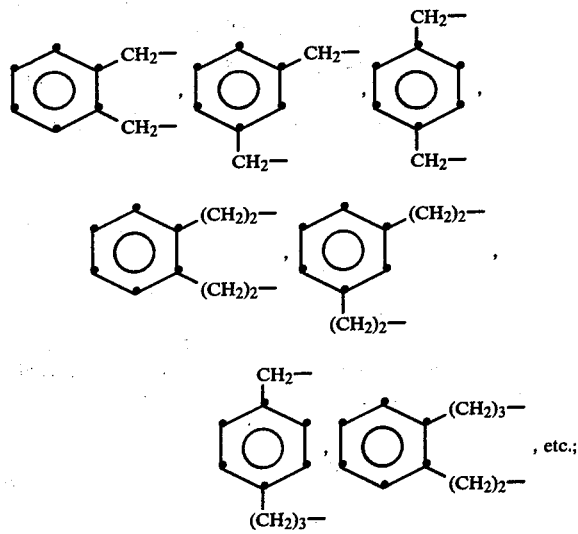

$C_6$-$C_{10}$ arylene is phenylene, tolylene, xylene, naphthylene etc.;

A bivalent group derived from 5- or 6-membered heterocycle is one derived from furan, thiophene, imidazole, oxazole, thiazole, pyrazole, pyrazine, pyridine, etc.;

$C_1$-$C_3$ alkoxy is methoxy, ethoxy, propoxy, isopropoxy, etc.;

In the prior art, this kind of histamine $H_2$ recept- or antagonist, cimetidine has been known [G. J. Durant, C. R. Ganellin et al., J. Med. Chem., 20, 901 (1977); German Pat. Nos. 2,344,779; 2,344,833].

The purpose of the present invention is to offer novel dicarboxylic diamides (I) which have an excellent histamine $H_2$ inhibiting action.

One of the objective compounds (I) represented by the formula (Ia) [in the formula (I), Q=R, Y=X, p=m, q=n], is produced according to the method as shown in the following equation.

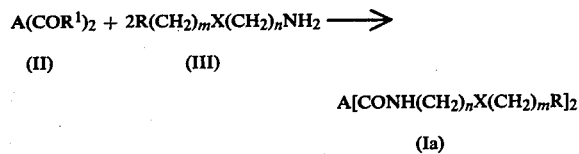

[wherein $R^1$ is hydroxy or reactive residue (for example, halogen, ester residue, mixed acid anhydride residue), and each of A, R, X, m and n has the same significance as mentioned above.]

That is, the starting amines (III) are reacted with acylating agents which include $A(CO-)_2$ to give the objective compounds (Ia). This acylation reaction may be conducted according to the conventional method, for example, the mixed acid anhydride method, acid halide method, acid/DCC method, etc. The method of acylation used in the present invention is concretely illustrated as follows.

(1) The mixed acid anhydride method

The mixed acid anhydride (II) of a carboxylic acid ($R^1$=mixed acid anhydride residue) is preliminarily prepared, with which amines (III) are reacted. The reaction is generally conducted under cooling at −30° C.-0° C. or at room temperature. In this reaction, the mixed acid anhydride is produced by reacting a carboxylic acid (IIa) (in II, $R^1$=OH) with an alkyl chlorocarbonate such as methyl chlorocarbonate or ethyl chlorocarbonate, under cooling at −30° C.-0° C. in the presence of a base such as triethylamine or pyridine in an inert solvent. As the solvents, tetrahydrofuran, methylene chloride, dioxane, dimethylsulfoxide, dimethylformamide, acetonitrile, hexaphosphoric triamide, etc. are used.

(2) The acid halide method

In the presence of a base such as triethylamine or pyridine, a carboxylic acid halide (IIb) (in II, $R^1$=Cl or Br) is reacted with amines (III). This reaction is conducted in a suitable solvent (for example, dimethylformamide, acetonitrile, hexamethylphosphoric triamide), under cooling at −20° C.-0° C. or at room temperature.

(3) The acid/DCC method

In the presence of DCC (dicyclohexylcarbodiimide), an acid (IIa) is reacted with amines (III) in a suitable solvent such as chloroform, dimethylformamide, or dimethylsulfoxide. This reaction may be conducted at room temperature or under cooling at −20° to −10° C.

The above objective compounds (Ia) can also be produced in an alternative method as follows.

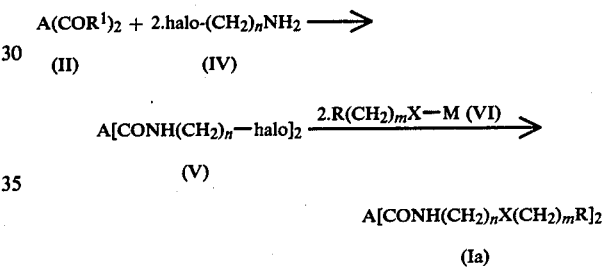

[wherein M is alkali metal (for example, sodium, potassium), halo is halogen, and each of A, R, $R^1$, X, m and n has the same significance as mentioned above.]

In the first step of this method, a haloalkylamine (IV) is reacted with a carboxylic acid or its reactive derivative (II) to form an intermediate (V). This acylation reaction may be carried out in the same condition as mentioned above. And then, the above intermediate (V) is condensed with an alkali metal compound (VI) to give the objective compound (Ia). This reaction may be conducted in a suitable solvent (for example, dimethylformamide, tetrahydrofuran, dimethylsulfoxide) under cooling at 0°-5° C. or at room temperature.

Further, the objective compounds (I) can also be produced in the method as shown in the following sequence.

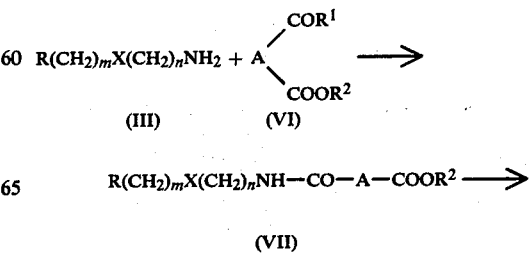

-continued

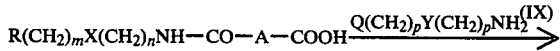

(VIII)

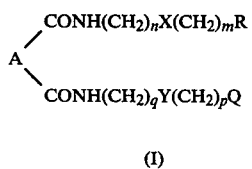

(I)

[wherein, $R^2$ is $C_1$–$C_3$ alkyl, and A, R, $R^1$, X, Y, Q, m, n, p and q have the same significance as mentioned above.]

In the first step, the amines (III) are acylated with a dicarboxylic acid (VI) in which one of the carboxy groups has been protected by esterification to give the ester compounds (VII). This acylation reaction may be conducted in the same condition as mentioned above. Alternatively, dicarboxylic anhydrides may be used instead of VI.

Subsequently, the ester compounds (VII) are hydrolyzed to give the carboxylic acids (VIII). Hydrolysis is conducted in an alcoholic solvent such as methanol and ethanol, under heating at boiling point of the solvent used in presence of an alkali (for example, alkali metal hydroxide such as sodium hydroxide and potassium hydroxide, alkali metal carbonate, alkali metal alkoxide).

The carboxylic acids (VIII) thus obtained are reacted with amines (IX) which are the same as or different from III to give the objective compounds (I). This acylation reaction may be conducted under the same condition as mentioned above.

Most of the starting amines and dicarboxylic acids are known and readily available.

The objective compounds (I) can be transformed into the pharmaceutically acceptable acid addition salts. As acid addition salts, those with inorganic acids (for example, hydrohalides, sulfates, nitrates, phosphates), and those with organic acids (for example, oxalates, acetates, citrates, lactates, maleates, succinates, tartrates, mandelates, methanesulfonates) are illustrated.

A preferable compound of this invention is a compound of the formula:

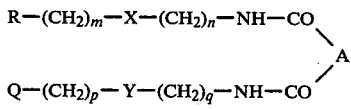

(wherein
A is $C_2$–$C_4$ alkylene, $C_2$–$C_4$ alkenylene, —$CH_2SCH_2$ or phenylene;
R and Q each is phenyl, thiazolyl, thienyl, or furyl respectively substituted by dimethylaminomethyl, 1-pyrrolidinylmethyl, or guanidino;
X and Y each is oxa or thia;
m and p each is 0 or 1; and
n and q each is 2 or 3).

The compounds of the formula (I) illustratively include

N,N'-bis{3-[3-(1-pyrrolidinylmethyl)phenoxy]propyl}trans-trans-muconamide;

N-{2-[(5-dimethylaminomethyl-2-thienyl)methylthio]ethyl}-N'-[3-(3-(1-pyrrolidinylmethyl)phenoxy)propyl]fumaramide;

N-{2-[(5-dimethylaminomethyl-2-furyl)methylthio]ethyl}-N'-{3-[3-(1-pyrrolidinylmethyl)phenoxy]propyl}fumaramide;

N,N'-bis{3-[3-(1-pyrrolidinylmethyl)phenoxy]propyl}fumaramide;

N,N'-bis{3-[3-(1-pyrrolidinylmethyl)phenoxy]propyl}isophthalamide;

N,N'-bis{3-[3-(1-pyrrolidinylmethyl)phenoxy]propyl}adipamide;

N,N'-bis{2-[(5-dimethylaminomethyl-2-furyl)methylthio]ethyl}fumaramide;

N,N'-bis{2-[(5-dimethylaminomethyl-2-furyl)methylthio]ethyl}isophthalamide;

N,N'-bis{2-[(5-dimethylaminomethyl-2-furyl)methylthio]ethyl}succinamide;

N,N'-bis{2-[(2-guanidino-4-thiazolyl)methylthio]ethyl}terephthalamide;

N,N'-bis{2-[(2-guanidino-4-thiazolyl)methylthio]ethyl}isophthalamide;

N,N'-bis{2-[(2-guanidino-4-thiazolyl)methylthio]ethyl}fumaramide;

N-{3-[3-(1-pyrrolidinylmethyl)phenoxy]propyl}-N'-{3-[3-(dimethylaminomethyl)phenoxy]propyl}fumaramide;

N-{3-[3-(1-pyrrolidinylmethyl)phenoxy]propyl}-N'-{2-[(2-guanidino-4-thiazolyl)methylthio]ethyl}fumaramide;

N-{3-[3-(1-pyrrolidinylmethyl)phenoxy]propyl}-N'-{2-[3-(dimethylaminomethyl)benzylthio]ethyl}fumaramide; and N-{2-[(5-dimethylaminomethyl-2-furyl)methylthio]ethyl}-N'-{2-[(2-guanidino-4-thiazolyl)methylthio]ethyl}fumaramide.

The compounds (I) in the present invention and their pharmaceutically acceptable acid addition salts bind to histamine $H_2$ receptor competitively with histamine to suppress the histamine $H_2$ effect. Therefore, the compounds (I) are useful in treatment of diseases which are improved by suppression of histamine $H_2$ effect, such as peptic ulcer.

The compounds (I) in the present invention or their pharmaceutically acceptable acid addition salts are administered to humans and animals orally or parenterally. They may be formulated into externally or internally applicable preparations together with diluent (for example, starch, sucrose, lactose, calcium carbonate, kaolin), bulking (for example, lactose, starch, calcium phosphate, kaolin, bentonite, talc), lubricant (for example, stearic acid, sodium benzoate), disintegrator (for example, starch, agar powder, carboxymethylcellulose, sodium alginate) and other pharmaceutical additive. As the formulation, solutions, suspensions, powders, granules, capsules, tablets, dry syrups, and injections are illustrated, and these formulations may be prepared in the conventional methods.

The compounds (I) or their pharmaceutically acceptable acid addition salts may be generally administered orally at two or three divided doses of 0.2–50 mg a day per 1 kg body weight in treatment of peptic ulcer. The dosage, however, may be suitably increased or decreased according to the state, clinical history, age, sex, etc. of the patient.

The examples of the present invention are shown as follows.

EXAMPLE 1

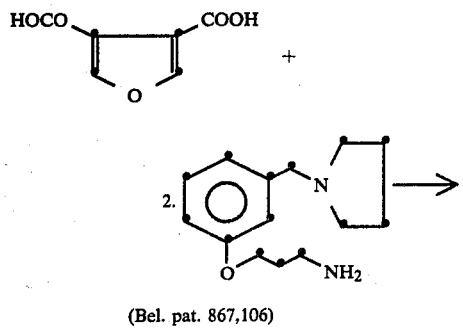

(Bel. pat. 867,106)

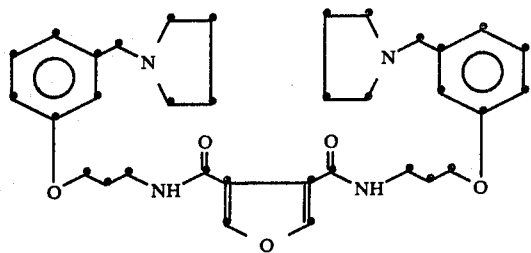

Preparation of
N,N′-bis{3-[3-(1-pyrrolidinylmethyl)phenoxy]propyl}-
3,4-furandicarboxydiamide (Method a):

To a solution of 3,4-furandicarboxylic acid (0.78 g) dissolved in dry tetrahydrofuran (80 ml) is added triethylamine (1.0 g) at −10° C., and then methyl chlorocarbonate (0.95 g) is added and stirred for 30 minutes. Then, a solution of 3-[3-(1-pyrrolidinylmethyl)phenoxy]propylamine (2.3 g) in dry tetrahydrofuran (30 ml) is added in dropwise fashion at −10° C., and the reaction mixture is slowly warmed up to room temperature, and stirred for 18 hours. The resulting precipitate is removed by filtration, and the filtrate is evaporated to dryness under reduced pressure. The residue is chromatographed on a column of silica gel (200 g) and eluted with ethyl acetate-methanol (20:5 V/V) to give the titled compound (1.29 g) (oily material). Yield: 22.9%.

NMR(CDCl$_3$): δ3.58 (4H,s), 4.07(4H,t,J=6 Hz), 8.02(2H,s), 8.97(2H,t,J=6 Hz).

The oily material obtained in the above is dissolved in ethanol, and a solution of oxalic acid (1.0 g) in ethanol is added, and then ether is added to crystallization. White crystals precipitated are collected by filtration and further recrystallized from 95% ethanol to give the dioxalate of the titled compound. mp 171°–172° dec.

Elementary analysis: C,58.75%, H,6.32%, N,7.03% (Calcd. for $C_{33}H_{42}N_4O_5.2(CO_2H)_2$: C,58.8%, H,6.14%, N,7.42%)

EXAMPLE 2

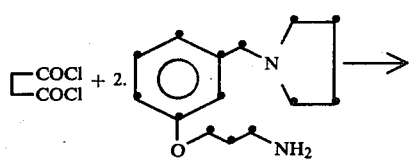

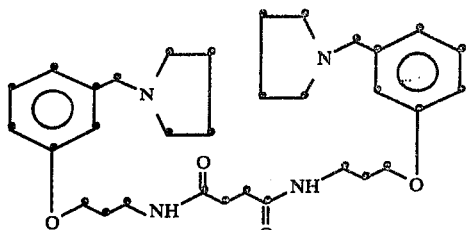

Preparation of
N,N′-bis{3-[3-(1-pyrrolidinylmethyl)phenoxy]propyl}-
succinamide (Method b):

To a solution of 3-[3-(1-pyrrolidinylmethyl)phenoxy]propylamine (0.7 g) and triethylamine (0.4 g) dissolved in dry dimethylformamide (5 ml) is added in dropwise fashion succinyl chloride (0.17 ml) at −10° C., and then the reaction mixture is slowly warmed up to room temperature, and stirred for 4 hours. The solvent is removed under reduced pressure, and the residue is distributed to ethyl acetate and saturated sodium hydrogencarbonate solution, and the organic layer is separated, dried on anhydrous sodium, sulfate and evaporated. The residue is chromatographed on a column of silica gel, the fractions eluted with methanol are removed, and the fractions eluted with methanol-conc. aqueous ammonia (50:1 (V/V)) solution give the titled compound (0.55 g) as an oily material. The oily material thus obtained is dissolved in ethanol, and a solution of oxalic acid (0.2 g) in ethanol is added. White crystals precipitated are collected by filtration and further recrystallized from an aqueous ethanol to give the oxalate of the titled compound. mp 157°–159° C.

Elementary analysis: C, 58.62%, H,6.95%, N,7.46% (Calcd. for $C_{32}H_{46}N_4O_4.2(CO_2H)_2 \cdot \frac{1}{2} H_2O$: C,58.44%, H,6.95%, N,7.57%)

EXAMPLE 3

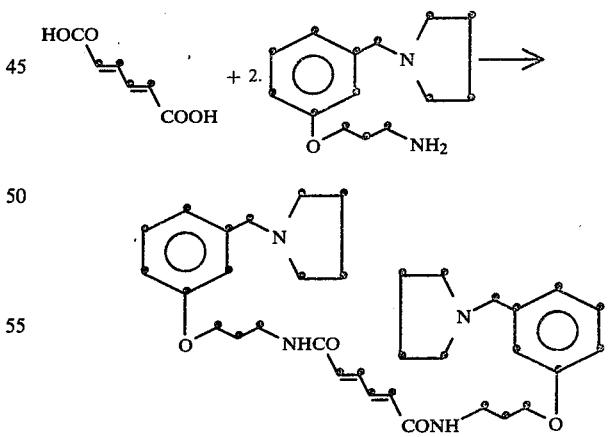

Preparation of
N,N′-bis{3-[3-(1-pyrrolidinylmethyl)phenoxy]propyl}-
trans-trans-muconamide (Method c):

To a solution consisting of trans-trans-muconic acid (0.28 g), tetrahydrofuran (20 ml) and hexamethylphosphoric triamide (4 ml) are added tiethylamine (0.4 g) and ethyl chlorocarbonate (0.43 g) at −28° C., and the mixture is stirred for 10 minutes. 3-[3-(1-pyrrolidinylmethyl)phenoxy]propylamine (0.94 g) is added thereto in dropwise fashion at −28° C., and the reaction mixture is gradually warmed up to room temperature and then stirred for 18 hours. After the solvent is removed under reduced pressure, the residue is distributed to ethyl acetate and saturated sodium hydrogencarbonate solution. The organic layer is dried on anhydrous sodium sulfate, and the solvent is removed. The residue is washed with ether to give the titled compound (0.65 g). Yield: 56.5%. mp 178°–180° C. (crystallized from methanol).

Elementary analysis: C, 70.76%, H,8.14%, N,9.61% (Calcd. for $C_{34}H_{46}N_4O_4$: C,71.05%, H,8.07%, N,9.61%).

EXAMPLE 4

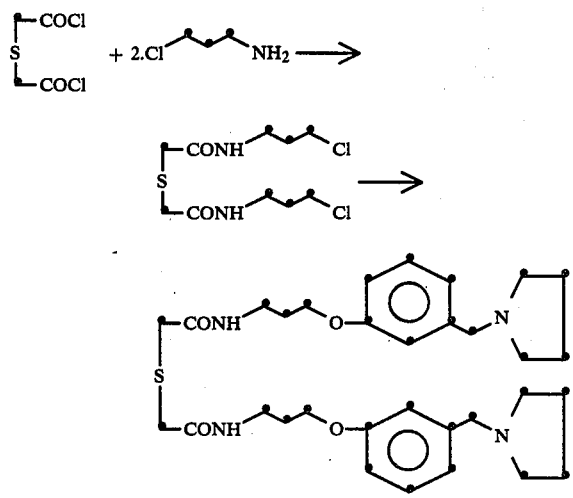

Preparation of N,N'-bis{3-[3-(1-pyrrolidinylmethyl)phenoxy]propyl}-thiodiglycoldamide (Method d):

To a solution of 3-chloropropylamine hydrochloride (5.2 g) and triethylamine (4.04 g) dissolved in dry dimethylformamide (10 ml) is added in dropwise fashion thiodiglycolyl chloride (1.87 g) at −5° C. to −10° C., and then the reaction mixture is slowly warmed up to room temperature and allowed to stand overnight. The reaction mixture is poured into water (10 ml), and extracted with ethyl acetate, and then the ethyl acetate layer is washed with water and dried on anhydrous sodium sulfate. Removal of ethyl acetate under reduced pressure gives white solid material as residue, which is washed with ether and collected by filtration to give N,N'-bis(3-chloropropyl)thiodiglycoldiamide (1.4 g, 46.7%).

50% Suspension of sodium hydride in mineral oil (200 mg) is suspended in dry dimethylformamide (5 ml), to which a solution of 3-(1-pyrrolidinylmethyl)phenol (740 mg) in dry dimethylformamide (5 ml) is added in dropwise fashion at 0°–5° C., and the reaction mixture is slowly warmed up to room temperature and stirred for 2 hours. To the solution thus obtained is added a solution of N,N'-bis(3-chloropropyl)thiodiglycoldiamide (627 mg) in dry dimethylformamide (5 ml) in dropwise fashion at 0°–5° C., and kept at room temperature overnight. The reaction mixture is poured into water (20 ml) and extracted with ethyl acetate. The ethyl acetate layer is washed with water and dried on anhydrous sodium sulfate, and then evaporated under reduced pressure. The residue is chromatographed on a column of silica gel, and eluted with methanol to give the titled compound (1 g) as an oily material. The oily material is dissolved in ethanol, and a solution of oxalic acid in ethanol is added. Precipitated crystals are collected by filtration and further recrystallized from ethanol to give the oxalate of the titled compound. mp 103°–105° C.

Elementary analysis: C,54.71%, H,6.44%, N,7.10%, S,4.34% (Calcd. for $C_{32}H_{46}N_4O_4S(COOH)_2.1\frac{1}{2}H_2O$: C,54.74%, H,6.76%, N,7.09%, S,4.06%)

EXAMPLE 5

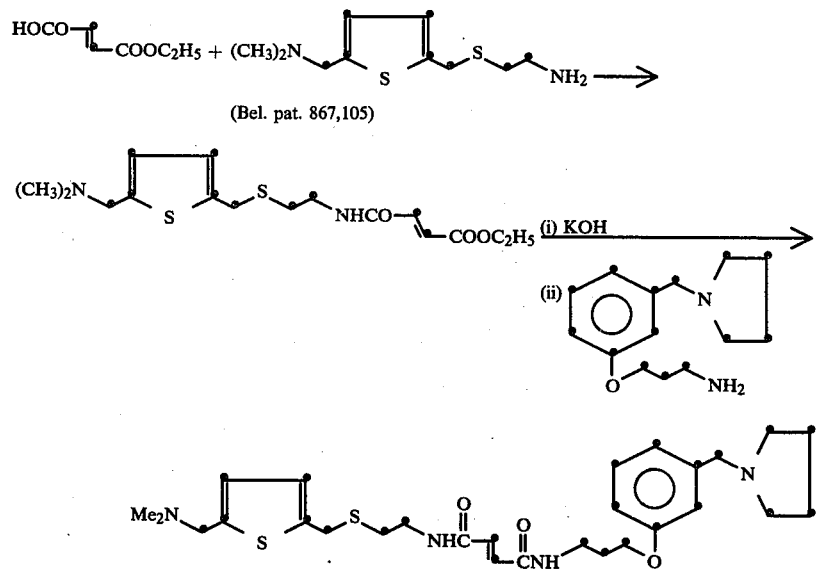

Preparation of N-2[(5-dimethylaminomethylthiophene-2-yl)-methylthio]ethyl-N'-[3-(3-(1-pyrrolidinylmethyl)phenoxy)-propyl]fumaramide (Method e):

To a solution of monoethyl fumarate (1.6 g) in dry tetrahydrofuran (20 ml) is added triethylamine (1.11 g) at 5° C. After stirring for 15 minutes at the above temperature, ethyl chlorocarbonate (1.19 g) is added thereto, and the resultant solution is stirred for 30 minutes at room temperature. Then, 5-dimethylaminomethyl-2-(2-aminoethyl)thiomethyl-thiophene (2.32 g) is added thereto at 5° C., and the reaction mixture is slowly warmed up to room temperature and then stirred for 4 hours. After termination of the reaction, tetrahydrofuran is distilled off under reduced pressure, and water is added to the residue. The mixture is extracted with chloroform, and the organic layer is washed with water, then dried and evaporated. The residue is chromatographed on a column of silica gel and eluted with methanol to give ethyl N-2-[(5-dimethylaminomethyl-thiophene-2-yl)methylthio]ethyl fumaraminate as an oily material. This oily material (841 mg) is dissolved in dry ethanol (4 ml), and 86% potassium hydroxide is added and stirred under heating at 80° C. for 30 minutes. The reaction mixture is cooled to lower than −20° C., and 16% hydrochloric acid-ethanol solution (2 ml) is added. Ethanol is distilled off at lower than 20° C., and dry tetrahydrofuran is added and evaporated under reduced pressure. The residue is suspended in tetrahydrofuran (30 ml), and triethylamine (477 mg) is added in dropwise fashion at 15° C. and the resultant solution is stirred for 30 minutes at the same temperature. Ethyl chlorocarbonate (257 mg) is added thereto in dropwise fashion at 5° C. and stirred for 30 minutes, and a solution of 3-[3-(1-pyrrolidinylmethyl)-phenoxy]propylamine (553 mg) dissolved in dry tetrahydrofuran (5 ml) is then added. The reaction mixture is slowly warmed up to room temperature and stirred for 4 hours. After termination of the reaction, tetrahydrofuran is distilled off under reduced pressure, and water is added to the residue. The mixture is extracted with chloroform, and the organic layer is washed with water, the dried and evaporated. The residue is chromatographed on a column of silica gel and eluted with methanol. The oily material thus obtained is treated with ether to give the titled compound (550 mg) as crystals. Recrystallization from ethyl acetate, mp 132°–134° C., NMR(CDCl$_3$): δ3.62(6H,s), 3.90(2H,s), 4.07(2H,t,J=6 Hz), IR(Nujol), ν$_{max}$ 3280(br), 1620 cm$^{-1}$.

Elementary analysis: C,61.49%, H,7.46%, N,9.91%, S,11.71% (Calcd. for C$_{28}$H$_{40}$N$_4$O$_3$S$_2$: C,61.73%, H,7.40%, N,10.28%, S,11.77%)

EXAMPLE 6

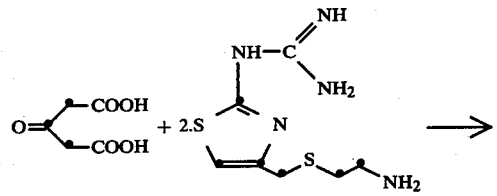

(Bel. pat. 866,156)

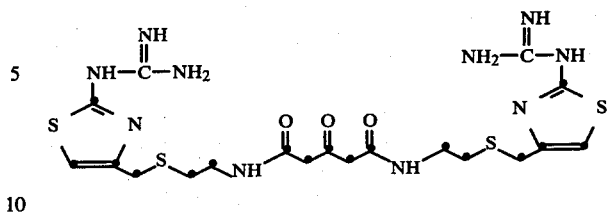

Preparation of N,N'-bis{2-[(2-guanidinothiazole-4-yl)methylthio]ethyl}-β-ketoglutardiamide (Method f):

To a solution of β-ketoglutaric acid (0.75 g) in dry tetrahydrofuran (60 ml), triethylamine (1.0 g) is added at −10° C. To the resultant solution are added dry hexamethylphosphoric triamide (5 ml) and methyl chlorocarbonate (0.95 g) sequentially at the above temperature. After stirring for 30 minutes, an additional amount of triethylamine (2.0 g) and 2-guanidino-4-(2-ethylamino-thiomethyl)thiazole dihydrochloride (3.0 g) are added, and the reaction mixture is slowly warmed up to room temperature, and stirred for 30 hours. After termination of the reaction, tetrahydrofuran is distilled off under reduced pressure, and 5% aqueous sodium hydrogencarbonate solution (about 100 ml) is added. The mixture is extracted with ethyl acetate, and the organic layer is washed with water, then dried and evaporated. The residue (1.73 g) is chromatographed on a column of silica gel, and eluted with methanol to give the titled compound (0.3 g).

NMR(CD$_3$OD): δ3.63(4H,s), 3.68(4H,s), 6.60(2H,s),

IR(film) ν$_{max}$ 3300(br), 1700, 1620(br), 1540 cm$^{-1}$.

The oily material obtained in the above is dissolved in ethanol, and a solution of maleic acid (0.3 g) in ethanol is added. Precipitated solids are collected by filtration and recrystallized from ethanol to give the maleate of the titled compound. mp 127°–128° C.

Elementary analysis: C,38.25%, H,4.40%, N,16.37%, S,14.98% (Calcd. for C$_{19}$H$_{28}$O$_3$N$_{10}$S$_4$.2C$_4$H$_4$O$_4$.2.5-H$_2$O: C,38.15%, H,4.86%, N,16,.48%, S,15.09%.

EXAMPLE 7

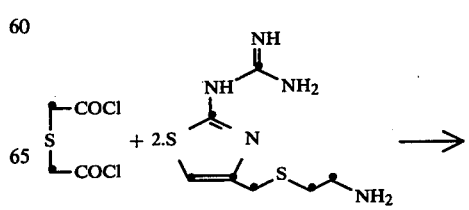

-continued

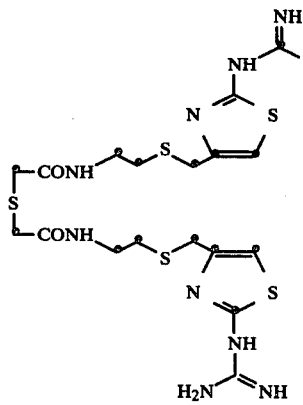

Preparation of
N,N'-bis{2-[(2-guanidinothiazole-4-yl)methylthio]ethyl}thiodiglycoldiamide (Method g):

2-Guanidino-4-(2-ethylaminothiomethyl)thiazole dihydrochloride (3.04 g) and triethylamine (4.5 g) are dissolved in dry dimethylformamide (6 ml). Thiodiglycolyl chloride (0.935 g) is added in dropwise fashion at −10° C., and the reaction mixture is slowly warmed up to room temperature and stirred for one hour. The solvent is distilled off under reduced pressure, and the residue is sufficiently washed with ethyl acetate and then dissolved in methanol. A solution of maleic acid in methanol is added in dropwise fashion at room temperature to yield white crystals as precipitate. This is collected by filtration and recrystallized from methanol to give the maleate of the titled compound. mp 97°–100° (d.).

Elementary analysis: C,37.45%; H,4.31%, N,16.87%, S,19.86% (Calcd. for $C_{18}H_{28}N_{10}O_2S_5.2C_4H_4O_4.H_2O$: C,37.76%, H,4.63%, N,16.94%, S,19.38%)

EXAMPLE 8

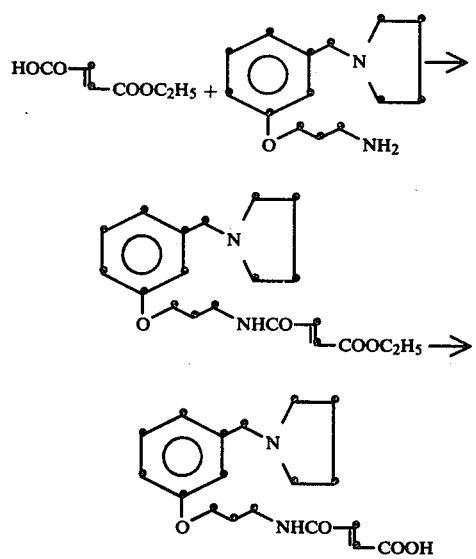

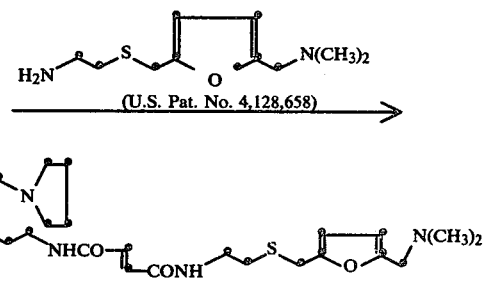

Preparation of
N-{2-[(5-dimethylaminomethylfuran-2-yl)methylthio]ethyl}-N'-{3-[3-(1-pyrrolidinylmethyl)phenoxy]propyl}-fumaramide (Method h):

Monoethyl fumarate (1.82 g) is dissolved in dry tetrahydrofuran (48 ml), and a solution (5 ml) of triethylamine (1.38 g) in dry tetrahydrofuran is added at −10° C., and sequentially a solution (5 ml) of ethyl chlorocarbonate (1.44 g) in dry tetrahydrofuran is added at the above temperature. After stirring for 15 minutes, a solution (30 ml) of 3-[3-(1-pyrrolidinyl methyl)phenoxy]propylamine (2.82 g) in dry tetrahydrofuran is added in dropwise fashion at −10° C. The reaction mixture is gradually warmed up to room temperature and stirred for 5 hours. The precipitate is filtered off and the filtrate is concentrated under reduced pressure. The residue is distributed to ethyl acetate and saturated sodium hydrogencarbonate aqueous solution, and the organic layer is dried on anhydrous sodium sulfae, and evaporated. The residue is crystallized on treatment with n-hexane to give ethyl N-{3-[3-(1-pyrrolidinylmethyl)phenoxy]-propyl}fumaraminate (3.6 g) melting at 78°–79° C. This substance (600 mg) is dissolved in ethanol (5 ml), and 86% potassium hydroxide (140 mg) is added and heated at 80° C. for 30 minutes. The reaction mixture is cooled to −10° C., and 16% hydrochloric acid-ethanol solution (2 ml) is added. White precipitate is filtrated off, and the filtrate is concentrated under reduced pressure. The residue is suspended in dry tetrahydrofuran (10 ml) and dry acetonitrile (5 ml), and triethylamine (500 mg) is added at −5° C., and sequentially ethyl chlorocarbonate (240 mg) is added at the above temperature. After stirring for 15 minutes, a solution (2 ml) of 5-dimethylaminomethyl-2-(2-aminoethylthiomethyl)furan (330 mg) in tetrahydrofuran is added in dropwise fashion. The reaction mixture is gradually warmed up to room temperature and stirred for 5 hours. White precipitate is filtrated off, and the filtrate is concentrated under reduced pressure, and then the residue is distributed to ethyl acetate-water. The organic layer is dried on anhydrous sodium sulfate, and the solvent is evaporated. The residue obtained in the above is chromatographed on a column of silica gel. The fractions eluted with methanol are removed, and the fractions eluted with methanol-conc. aqueous ammonia (50:1 (V/V)) solution are collected and evaporated. The residue is crystallized from ethyl acetate to give the titled compound (200 mg) melting at 126°–128° C. Yield: 21.7%.

NMR(CDCl$_3$): δ2.27(6H,s), 3.42(2H,s), 3.58(2H,s), 3.68(2H,s), 4.03(2H,t,J=6 Hz), 6.1(2H,s), 6.63–7.67(6H,m).

IR(Nujol) $\nu_{max}$ 3270, 3050, 1620, 1580 cm$^{-1}$.

Elementary analysis: C,63.04%, H,7.69%, N,10.69%, S,6.31% (Calcd. for $C_{28}H_{40}N_4O_4S$: C,63.61%, H,7.63%, N,10.60%, S,6.06%)

EXAMPLE 9

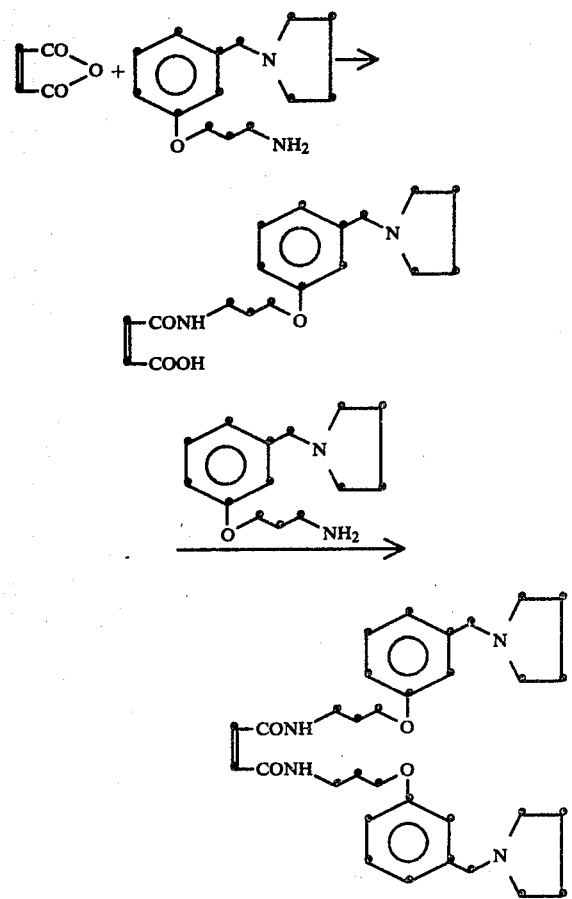

Preparation of N,N'-bis[3-[3-(1-pyrrolidinylmethyl)phenoxy]propyl]-maleamide (Method i):

Maleic anhydride (1,96 g) is added to a solution of 3-[3-(1-pyrrolidinylmethyl)phenoxy]propylamine (4.6 g) in dry tetrahydrofuran, and the resultant solution is stirred at room temperature for 20 hours. After adding hexamethylphosphoric triamide (14 ml), the reaction mixture is cooled to $-10°$ C., and triethylamine (2.4 g) and methyl chlorocarbonate (1.9 g) are sequentially added thereto, and stirred for 30 minutes at the above temperature. Then, 3-[3-(1-pyrrolidinylmethyl)phenoxy]propylamine (4.9 g) is added, and the mixture is slowly warmed up to room temperature and then stirred for 16 hours. The precipitate is filtrated off, and the filtrate is concentrated under reduced pressure, and the residue is distributed to ethyl acetate-saturated sodium hydrogencarbonate aqueous solution. The organic layer is washed with water, dried, and evaporated, and the residue (9.4 g) is chromatographed on a column of silica gel (200 g) and eluted with methanol-conc. aqueous ammonia (50:1 V/V) solution to give the titled compound (5.1 g) as an oily material. Yield: 47%.

NMR(CDCl$_3$); δ4.03(4H,t,J=6 Hz), 6.06(2H,s), 8.83(2H,t,J=6 Hz).

The oily material obtained in the above is dissolved in ethanol, to which a solution of oxalic acid in ethanol is added, and then ethyl acetate is added to give crystals. White precipitated crystals are collected by filtration, and further recrystallized from 95% ethanol-ethyl acetate to give the dioxalate of the titled compound. mp 106°–108° C.(decomposition).

Elementary analysis: C,58.56%, H,6.82%; N,7.48% (Calcd. for $C_{32}H_{44}N_4O_4.2(CO_2H)_2.\frac{1}{2}H_2O$: C,58.60%, H,6.69%, N,7.59%)

In the following tables, the column of the process means that the reaction of each example is conducted under the condition shown in the corresponding process of the above-disclosed example.

TABLE 1

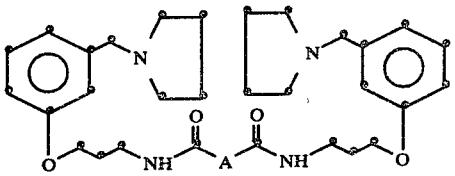

| Example No. | Process | A | Salt | mp (°C.) | Infrared Absorption Spectrum $v_{max}$ cm$^{-1}$ | Nuclear Magnetic Resonance Spectrum δ |
|---|---|---|---|---|---|---|
| 10 | a | —CH=CH— (trans) | — | 165–167° | 3280, 3050, 1620, 1580. (Nujol) | — |
| 11 | a | ⟨phenyl⟩ | — | 154–156° | 3280, 1635(sh) 1620. (Nujol) | 2.0(4H,t,J=6Hz), 3.53(4H,s), 4.03(4H,t,J=6Hz), 6.03–7.33 (8H,m), 7.90(4H,s), 8.67(2H, br,t) (in d$_6$DMSO) |
| 12 | d | —CH$_2$SCH$_2$— | 2(COOH)$_2$.1½H$_2$O | 103–105° | 3250, 1650 (film, free base) | 3.23(4H,s), 3.58(4H,s), 4.05(4H,t,J=5Hz)(CDCl$_3$, free base) |
| 13 | c | ⟨pyridyl 2,6⟩ | — | 80–82° | 3250, 1670, 1640 1595. (Nujol) | 2.11(4H,t,J=6Hz), 3.55(4H,s), 3.65(4H,t,J=6Hz), 4.08(4H,t, J=6Hz), 6.67–7.33(8H,m), 7.93 –8.47(3H,m)(CD$_3$OD) |

TABLE 1-continued

[Structure shown at top of table]

| Example No. | Process | A | Salt | mp (°C.) | Infrared Absorption Spectrum $\nu_{max}$ cm$^{-1}$ | Nuclear Magnetic Resonance Spectrum δ |
|---|---|---|---|---|---|---|
| 14 | h | [meta-phenylene] | 2(CO$_2$H)$_2$·½H$_2$O | 135–140° | — | 2.10(4H,t,J=6Hz), 3.57(4H,s), 4.07(4H,t,J=6Hz), 6.67–8.40 (12H,m)(CD$_3$OD, free base) |
| 15 | a | [cyclobutane-1,3-diyl] | 2(COOH)$_2$ | 159–161° | — | 3.60(4H,s), 4.03(4H,t,J=6Hz), (in CDCl$_3$, free base) |
| 16 | a | —CH$_2$CH$_2$CH—<br>                  │<br>                  NH$_2$ | 3(CO$_2$H)$_2$ | 119–120° | — | — |
| 17 | c | [pyridine-2,6-diyl] | 2(CO$_2$H)$_2$ | 166–168° | — | 2.10(4H,t,J=6Hz), 3.57(4H,s), 4.08(4H,t,J=6Hz), 6.58–7.35 (8H,m), 7.73(2H,br,t), 8.52(1H,m), 9.08(2H,m)(in, CDCl$_3$, free base) |
| 18 | a | —(CH$_2$)$_4$— | — | 106–108° | — | 3.57(4H,s), 4.00(4H,t,J=6Hz), 6.10(2H,b)(CDCl$_3$) |
| 19 | a | [xylylene —CH$_2$-C$_6$H$_4$-CH$_2$—] | 2(CO$_2$H)$_2$ H$_2$O | 98–100° | — | 3.57(8H,s), 3.95(4H,t,J=6Hz), (CDCl$_3$, free base) |
| 20 | a | >C(C$_2$H$_5$)$_2$ | 2(COOH)$_2$ 2H$_2$O | 98–100° | — | 1.23(6H,t,J=Hz), 3.58(4H,s), 4.03(4H,t,J=6Hz), 4.12(4H,q, J=7Hz)(CDCl$_3$, free base) |
| 21 | c | [cyclohexane-1,4-diyl] (1,4-trans) | — | 167–168° | 3260, 1620, 1575. | 3.57(4H,s), 4.0(4H,t,J=6Hz) (CDCl$_3$) |
| 22 | b | single bond | — | 94–96° | — | 2.05(4H,t,J=7Hz), 3.60(4H,s), 4.05(4H,t,J=7Hz), 6.67–7.37 (8H,m), 7.87(2H,br,t)(CDCl$_3$) |

TABLE 2

[Structure: Me$_2$N—[ring]—O—S—NH—A—NH—S—O—[ring]—NMe$_2$]

| Example No. | Process | A | Salt | mp (°C.) | Nuclear Magnetic Resonance Spectrum δ(CDCl$_3$) |
|---|---|---|---|---|---|
| 23 | a | —CH=CH— (trans) | — | 146–148° | 2.27(12H,s), 3.45(4H,s), 3.72 (4H,s), 6.13(4H,s), 7.07(2H,s) |
| 24 | c | [pyridine-3,5-diyl] | 2(COOH)$_2$·H$_2$O | 124–127° | 2.17(12H,s), 3.37(4H,s), 3.73 (4H,s), 6.08(4H,s) (free base) |
| 25 | b | [phenylene] | 2(COOH)$_2$ | 123–125° | 2.20(12H,s), 3.38(4H,s), 3.75 (4H,s), 6.13(4H,s) (free base) |
| 26 | b | —CH$_2$—CH$_2$— | — | 82–83° | 2.25(12H,s), 2.50(4H,s), 3.40 (4H,s), 3.70(4H,s), 6.10(4H,s) |

TABLE 2-continued

Me₂N−[furan ring]−O−...−S−...−NH−CO−A−CO−NH−...−S−...−[furan ring]−O−NMe₂

| Example No. | Process | A | Salt | mp (°C.) | Nuclear Magnetic Resonance Spectrum δ(CDCl₃) |
|---|---|---|---|---|---|
| 27 | a | [cyclobutane] | 2(COOH)₂·½H₂O | 117–121° | 2.25(12H,s), 3.43(4H,s), 3.73 (4H,s), 6.15(4H,s) (free base) |
| 28 | b | [benzene ring] | — | 129–131° | 2.22(12H,s), 3.37(4H,s), 3.73 (4H,s), 6.08(4H,s), 7.73(4H,s) |
| 29 | b | —CH₂SCH₂— | 2(COOH)₂ | 87–89° | 2.23(12H,s), 3.23(4H,s), 3.40 (4H,s), 3.70(4H,s), 6.07(4H,s) (free base) |
| 30 | i | —CH=CH— (cis) | 2(CO₂H)₂·4H₂O | 130–133° (decomp.) | 2.25(12H,s), 3.45(4H,s), 3.73 (4H,s), 6.13(2H,s), 6.17(2H,s) (free base) |
| 31 | b | single bond | — | 76–78° | 2.27(12H,s), 3.43(4H,s), 3.73 (4H,s), 6.15(4H,s) (CDCl₃) |

TABLE 3

R⁴−[thiophene with R³]−S−...−NH−CO−A−CO−NH−...−S−[thiophene with R³]−R⁴

| Example No. | Process | A | R³ | R⁴ | Salt | mp (°C.) | Infrared Absorption Spectrum ν_max cm⁻¹ | Nuclear Magnetic Resonance Spectrum δ(CDCl₃) |
|---|---|---|---|---|---|---|---|---|
| 32 | c | [pyridine ring] | i-Pr | —N[pyrrolidine] | 2.5(COOH)₂ | 157–160° (decomp.) | — | 1.17(12H,d,7Hz), 3.70(4H,s), 3.87(4H,s), 6.68(2H,s) (free base) |
| 33 | b | —CH₂SCH₂— | H | —N(Me)Me | — | 76–78° | 3260, 1650. (Nujol) | 3.25(4H,s), 3.57(4H,s), 3.90 (4H,s) |
| 34 | b | single bond | H | —N(Me)Me | — | 70–72° | — | 2.27(12H,s), 3.57(4H,s), 3.90 (4H,s), 7.70(2H,b) |

TABLE 4

[benzene-CH₂NMe₂]−...−S−...−NH−CO−A−CO−NH−...−S−...−[Me₂NCH₂-benzene]

| Example No. | Process | A | Salt | mp (°C.) | Infrared Absorption Spectrum ν_max cm⁻¹ | Nuclear Magnetic Resonance Spectrum δ(CDCl₃) |
|---|---|---|---|---|---|---|
| 35 | b | —CH=CH— (trans) | — | 138–140° | — | 2.23(12H,s), 3.38(4H,s), 3.70 (4H,s), 6.97(2H,s) |
| 36 | b | [benzene ring] | 2(COOH)₂·H₂O | 105–109° | — | 2.22(12H,s), 3.43(4H,2), 3.75 (4H,s) (free base) |

TABLE 4-continued

[Structure: bis(dimethylaminobenzyl-S-CH₂CH₂-NH-CO-A-CO-NH-CH₂CH₂-S-benzyl-dimethylamino)]

| Example No. | Process | A | Salt | mp (°C.) | Infrared Absorption Spectrum $\nu_{max}$ cm$^{-1}$ | Nuclear Magnetic Resonance Spectrum δ(CDCl₃) |
|---|---|---|---|---|---|---|
| 37 | b | (para-phenylene) | — | 148–150° | 3250, 1620. (Nujol) | 2.22(12H,s), 3.40(4H,s), 3.75 (4H,s), 6.67(2H,br) (free base) |
| 38 | b | —CH₂SCH₂— | 2(COOH)₂ | 124–127° (decomp.) | 3260(br), 1650(br) (film, free base) | 2.25(12H,s), 3.27(4H,s), 3.43 (4H,s), 3.77(4H,s) (free base) |

Note
Production of the starting amine:

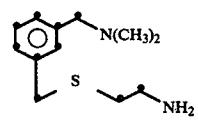

(Bel. pat. 867,106)

TABLE 5

[Structure: bis(guanidino-thiazolyl-CH₂-S-CH₂CH₂-NH-CO-A-CO-NH-CH₂CH₂-S-CH₂-thiazolyl-guanidino)]

| Example No. | Process | A | Salt | mp (°C.) | Infrared Absorption Spectrum $\nu_{max}$ cm$^{-1}$ | Nuclear Magnetic Resonance Spectrum δ(d₆-DMSO) |
|---|---|---|---|---|---|---|
| 39 | f | (pyridine) | — | 240–241° (decomp.) | — | 6.95(8H,brs), 7.13(2H,s), 10.70(2H,s) |
| 40 | b | (phenylene) | 2C₂H₅OH ½H₂O | 203–206° (decomp.) | — | 3.65(4H,s), 6.52(2H,s) |
| 41 | b | (phenylene) | 1.5(COOH)₂ | 230–243° (decomp.) | — | (free base) 3.65(4H,s), 6.52(2H,s) |
| 42 | b | —CH=CH— (trans) | H₂O | 180–189° (decomp.) | — | 3.57(4H,s), 6.48(2H,s) |
| 43 | b | —CH₂SCH₂— | 2C₄H₄O₄· H₂O— | 97–100° (decomp.) | 1630(Nujol) | 3.23(4H,s), 3.75(4H,s), 7.02(2H,s) (d₆-DMSO) |
| 44 | b | —CH₂CH₂— | ½C₂H₅OH | 160–175° (decomp.) | — | 2.30(4H,s), 3.60(4H,s), 6.47(2H,s) |

TABLE 6

Me₂N−[ring: S]−CH₂−S−CH₂CH₂−NH−CO−A−CO−NHB

| Example No. | Process | A | B | Salt | mp (°C.) | Infrared Absorption Spectrum $\nu_{max}$ cm$^{-1}$ | Nuclear Magnetic Resonance Spectrum δ |
|---|---|---|---|---|---|---|---|
| 45 | e | —CH=CH— (trans) | —(CH₂)₂SCH₂−[oxazole ring]−CH₂N(Me)(Me) | 3(COOH)₂ ½H₂O | 81–6° | 3270(br), 1620 (film, free base) | 2.27(12H,s), 6.08(2H,s), (CDCl₃, free base) |
| 46 | e | —CH=CH— (trans) | —CH₂Ph | (COOH)₂ H₂O | 184–190° (decomp.) | 3260(br), 1630 (Nujol, free base) | 2.28(6H,s), 3.63(2H,s), 3.88 (2H,s), 3.90(2H,s) (CDCl₃ + CD₃OD) (free base) |
| 47 | e | —[phenyl ring]— | —(CH₂)₂SCH₂−[oxazole ring]−CH₂N(Me)(Me) | — | 129–131° | — | 2.17(6H,s), 2.23(6H,s), 3.37 (2H,s), 3.52(2H,s), 3.72(2H,s), 3.88(2H,s), 6.10(2H,s), 7.77(4H,s) (CDCl₃) |
| 48 | e | —CH=CH— (trans) | [phenyl ring with CH₂N(Me)(Me) and —(CH₂)₂SCH₂—] | 2(COOH)₂ 2H₂O | 112–115° (decomp.) | 3260(br), 1640(br) (film, free base) | 2.23(6H,s), 2.27(6H,s), 3.57 (2H,s), 3.72(2H,s), 3.88(2H, s) |

TABLE 7

[Structure: pyrrolidine-N-CH₂-phenyl-O-(backbone)-NH-C(=O)-A-C(=O)-NHB]

| Example No. | Process | A | B | Salt | mp (°C.) | Infrared Absorption Spectrum $\nu_{max}$cm$^{-1}$ | Nuclear Magnetic Resonance Spectrum δ |
|---|---|---|---|---|---|---|---|
| 49 | h | —CH=CH— (trans) | 3-(CH₂)₃-phenyl-N(CH₃)₂ | — | 171–172° | 3275, 3050, 1620, 1580 (Nujol) | 2.2(6H,s), 4.0(4H,t,J=5Hz), 6.67–7.33(m,10H), 7.53(br, m,2H) (CDCl₃) |
| 50 | h | phenyl (para-Me₂N-CH₂-) | furan-CH₂-S-(CH₂)₂- | — | 115–116° | 3270, 1620, 1580 (Nujol) | 2.18(6H,s), 3.38(2H,s), 3.57(2H,s), 3.73(2H,s), 4.10(2H, t,J=6Hz), 6.10(2H,s), 7.73(4H,s) (CDCl₃) |
| 51 | h | —CH=CH— (trans) | 2-guanidino-thiazole-CH₂-S(CH₂)₂- | — | 186–188° | — | 3.50(2H,s), 3.60(2H,s), 3.97(2H,t,J=6Hz), 6.43(1H,s) (DMSO) |
| 52 | h | phenyl (para-Me₂N-CH₂-) | thiophene-CH₂-S—(CH₂)₂- | — | 120–121° | 3270, 1625, 1580. (Nujol) | 2.23(6H,s), 3.53(2H,s), 3.56(2H,s), 3.90(2H,s), 4.10(2H, t,J=6Hz), 7.70(4H,s) (CDCl₃) |
| 53 | h | —CH=CH— (trans) | phenyl(Me₂N-CH₂-)-S—(CH₂)₂- | 2(CO₂H)₂·½H₂O | 188–190° | — | 2.22(6H,s), 3.37(2H,s), 3.57(2H,s), 3.68(2H,s), 3.98(2H, t,J=6Hz) (CDCl₃, free base) |

TABLE 7-continued
| Example No. | Process | A | B | Salt | mp (°C.) | Infrared Absorption Spectrum $\nu_{max}$cm$^{-1}$ | Nuclear Magnetic Resonance Spectrum δ |
|---|---|---|---|---|---|---|---|
| 54 | h | —CH=CH— (trans) | 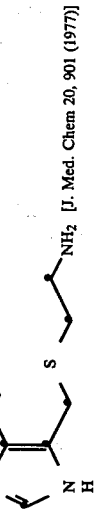 | — | 168–170° | 3250; 1615, 1575. (Nujol) | 2.20(3H,s), 3.57(2H,s), 3.70 (2H,s), 4.02(2H,t,J=6Hz), 7.43(1H,s) (CD$_3$OD) |
(Note)
Production of the starting amine:
[structure] NH$_2$ [J. Med. Chem 20, 901 (1977)]

TABLE 8

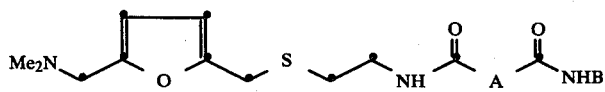

| Example No. | Process | A | B | Salt | mp (°C.) | Nuclear Magnetic Resonance Spectrum δ |
|---|---|---|---|---|---|---|
| 55 | h | —CH=CH— (trans) | —(CH₂)₃—O—C₆H₄—NMe₂ | 2(COOH)₂·H₂O | 139–143° | 2.22(3H,s), 2.23(3H,s), 3.40 (2H,s), 3.70(2H,s), 6.10(2H, s) (CDCl₃) |
| 56 | h | phenyl | —(CH₂)₂—S—C₆H₄—NMe₂ | — | 129–131° | 2.22(12H,s), 3.42(4H,s), 3.78 (4H,s), 6.18(2H,s), 7.83(4H, s), (CDCl₃) |
| 57 | h | phenyl | —CH₂CH₂—phenyl | — | 157–159° | 2.18(6H,s), 3.37(2H,s), 3.73 (2H,s), 6.10(2H,s), 7.23(5H, s), 7.67(4H,s) (CDCl₃) |
| 58 | h | —CH=CH— (trans) | —(CH₂)₂—S—CH₂—thiazole-NH—C(=NH)NH₂ | — | 166–168° | 2.23(6H,s), 3.40(2H,s), 3.62 (2H,s), 3.70(2H,s), 6.10(2H, s), 6.33(1H,s), 6.88(2H,s). (CDCl₃ + d₆DMSO) |

(Note)
Production of the starting amine:

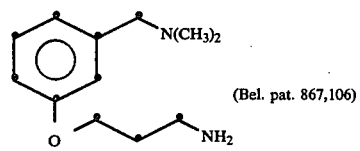

(Bel. pat. 867,106)

TABLE 9

Me₂N—C₆H₄—O—(CH₂)...NHCOCONH...(CH₂)—O—C₆H₄—NMe₂

| Example No. | Process | A | Salt | mp (°C.) | Nuclear Magnetic Resonance Spectrum δ |
|---|---|---|---|---|---|
| 59 | b | single bond | — | 87–89° | 2.23(12H,s), 3.38(4H,s), 4.05 (4H,t,J = 6Hz), 7.83(2H,b) (CDCl₂) |

(Note)
The symbols in the table have the following significances: Me = methyl, Ph = phenyl, i-Pr = isopropyl In the table 10, the symbol pA₂ indicates the degree of pulse inhibition of the compounds (I) in the present invention in the enucleated atrium of a guinea pig. The assigned number of compounds in the table conforms to the number of the examples.

TABLE 10

| Compound No. | Salt | pA₂ |
|---|---|---|
| 10 | — | 7.27 |
| 11 | — | 6.69 |
| 12 | 2(COOH)₂·1½H₂O | 7.18 |
| 14 | 2(COOH)₂·½H₂O | 7.22 |
| 34 | 2C₂H₅OH·½H₂O | 7.19 |
| 36 | H₂O | 8.0 |
| cimetidine | | 6.63 |

(Note) PA₂ is an in vitro indicator of histamine H₂-blocking effect. The pulse of the enucleated atrium of a guinea pig was increased on treatment with histamine, and the competition effect of histamine on the atrium preliminarily treated with the drugs was observed. The result was shown by negative logarithms of the dose of antagonist which is required to shift the dose-response curve of histamine in parallel to the side corresponding to a doubling of the concentration of histamine [Ariens, Molecular Pharmacology, vol./, Academic Press, New York (1964)].

What we claim is:
1. A compound of the formula:

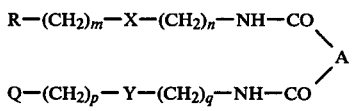

(wherein

A is C$_2$-C$_4$ alkylene, C$_2$-C$_4$ alkenylene, —CH$_2$SCH$_2$ or phenylene;

R and Q each is phenyl, thiazolyl, thienyl, or furyl respectively substituted by dimethylaminomethyl, 1-pyrrolidinylmethyl, or guanidino;

X and Y each is oxa or thia;

m and p each is 0 or 1; and n and q each is 2 or 3).

2. A compound according to claim 1, namely N,N'-bis{3-[3-(1-pyrrolidinylmethyl)phenoxy]propyl}-trans-trans-muconamide.

3. A compound according to claim 1, namely N-{2-[(5-dimethylaminomethyl-2-thienyl)methylthio]ethyl}-N'-[3-(3-(1-pyrrolidinylmethyl)phenoxy)propyl]-fumaramide.

4. A compound according to claim 1, namely N-{2-[(5-dimethylaminomethyl-2-furyl)methylthio]ethyl}-N'-{3-[3-(1-pyrrolidinylmethyl)phenoxy]propyl}-fumaramide.

5. A compound according to claim 1, namely N,N'-bis{3-[3-(1-pyrrolidinylmethyl)phenoxy]propyl}-fumaramide.

6. A compound according to claim 1, namely N,N'-bis{3-[3-(1-pyrrolidinylmethyl)phenoxy]propyl}isophthalamide.

7. A compound according to claim 1, namely N,N'-bis{3-[3-(1-pyrrolidinylmethyl)phenoxy]propyl}adipamide.

8. A compound according to claim 1, namely N,N'-bis{2-[(5-dimethylaminomethyl-2-furyl)methylthio]ethyl}fumaramide.

9. A compound according to claim 1, namely N,N'-bis{2-[(5-dimethylaminomethyl-2-furyl)methylthio]ethyl}isophthalamide.

10. A compound according to claim 1, namely N,N'-bis{2-[(5-dimethylaminomethyl-2-furyl)methylthio]ethyl}succinamide.

11. A compound according to claim 1, namely N,N'-bis{2-[(2-guanidino-4-thiazolyl)methylthio]ethyl}-terephthalamide.

12. A compound according to claim 1, namely N,N'-bis{2-[(2-guanidino-4-thiazolyl)methylthio]ethyl}isophthalamide.

13. A compound according to claim 1, namely N,N'-bis{2-[(2-guanidino-4-thiazolyl)methylthio]ethyl}-fumaramide.

14. A compound according to claim 1, namely N-{3-[3-(1-pyrrolidinylmethyl)phenoxy]propyl}-N'-{3-[3-(dimethylaminomethyl)phenoxy]propyl}fumaramide.

15. A compound according to claim 1, namely N-{3-[3-(1-pyrrolidinylmethyl)phenoxy]propyl}-N'-{2-[(2-guanidino-4-thiazolyl)methylthio]ethyl}fumaramide.

16. A compound according to claim 1, namely N-{3-[3-(1-pyrrolidinylmethyl)phenoxy]propyl}-N'-{2-[3-(dimethylaminomethyl)benzylthio]ethyl}fumaramide.

17. A compound according to claim 1, namely N-{2-[(5-dimethylaminomethyl-2-furyl)methylthio]ethyl}-N'-{2-[(2-guanidino-4-thiazolyl)methylthio]ethyl}-fumaramide.

* * * * *

UNITED STATES PATENT AND TRADEMARK OFFICE
CERTIFICATE OF CORRECTION

PATENT NO. : 4,433,154
DATED : Feb. 21, 1984
INVENTOR(S) : Kentaro HIRAI

It is certified that error appears in the above-identified patent and that said Letters Patent is hereby corrected as shown below:

Cover page, column 1, between the lines designated [22] and [51], please add the following:
--[30] Foreign Application Priority Data Dec. 19, 1980 [JP] Japan..............180798/1980--;

Column 1, line 11, change "cimetidene" to --cimetidine--;

Column 2, lines 1 and 2, formula (I), change:

"R-$(CH_2)_m$-X-$(CH_2)_n$-NH-CO
                                    A
Q-$(CH_2)_p$-Y-$(CH_2)_q$-NH-CO      "      to:

--R-$(CH_2)_m$-X-$(CH_2)_n$-NH-CO
                                    A
Q-$(CH_2)_p$-Y-$(CH_2)_q$-NH-CO      --;

Column 7, line 52, change "crystallization" to --crystallize--;
Column 8, line 26, change "sodium, sulfate" to --sodium sulfate,--;
Column 9, Example 4, line 2 under "Preparation of", change "thiodiglycoldamide" to --thiodiglycoldiamide--;
Column 12, line 30, change "30" to --20--;

Column 14, line 10, change:

" 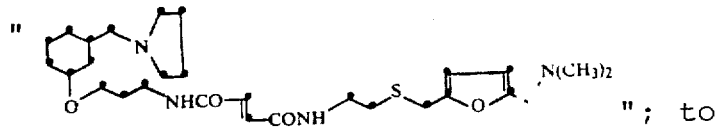 "; to

UNITED STATES PATENT AND TRADEMARK OFFICE
CERTIFICATE OF CORRECTION

PATENT NO. : 4,433,154

DATED : Feb. 21, 1984

INVENTOR(S) : Kentaro HIRAI

It is certified that error appears in the above-identified patent and that said Letters Patent is hereby corrected as shown below:

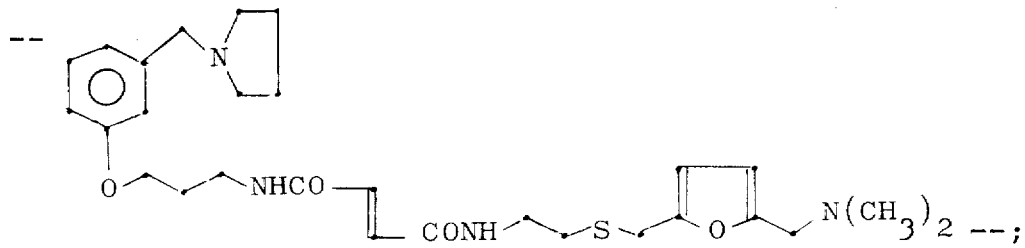

Column 14, line 34, change "sulfae" to --sulfate--;

Columns 17 and 18, Table 1, line 2, change the formula from:

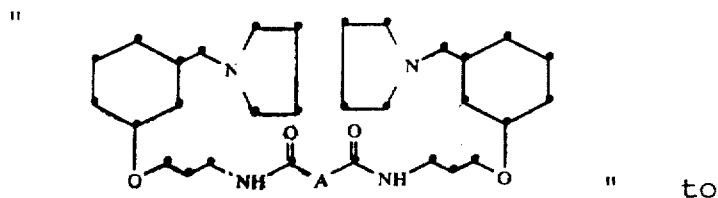 to

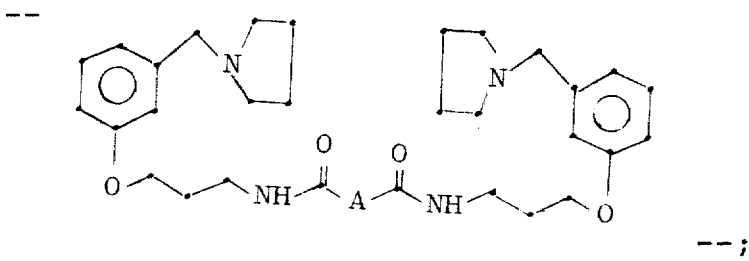

--;

UNITED STATES PATENT AND TRADEMARK OFFICE
CERTIFICATE OF CORRECTION

PATENT NO. : 4,433,154

DATED : Feb. 21, 1984

INVENTOR(S) : Kentaro HIRAI

It is certified that error appears in the above-identified patent and that said Letters Patent is hereby corrected as shown below:

Columns 19 and 20, Table 4, Example 36, change "3.43 (4H,2)" to --3.43 (4H,s)--;

Columns 23 and 24, Table 6, Example 45, change "81 - 6" to --81 - 86--.

Signed and Sealed this

Twenty-sixth Day of February 1985

[SEAL]

Attest:

DONALD J. QUIGG

Attesting Officer

Acting Commissioner of Patents and Trademarks